United States Patent [19]
Boyce

[11] Patent Number: 5,976,878
[45] Date of Patent: *Nov. 2, 1999

[54] METHOD AND APPARATUS FOR PREPARING COMPOSITE SKIN REPLACEMENT

[75] Inventor: Steven Boyce, San Diego, Calif.

[73] Assignee: The Regents of the University of California, Oakland, Calif.

[ * ] Notice: This patent is subject to a terminal disclaimer.

[21] Appl. No.: 08/376,293

[22] Filed: Jan. 23, 1995

Related U.S. Application Data

[60] Continuation of application No. 08/052,167, Apr. 23, 1993, abandoned, which is a division of application No. 07/759,641, Sep. 12, 1991, Pat. No. 5,273,900, which is a continuation of application No. 07/398,297, Aug. 24, 1989, abandoned, which is a continuation of application No. 07/186,603, Apr. 27, 1988, abandoned, which is a continuation-in-part of application No. 07/043,321, Apr. 28, 1987, abandoned.

[51] Int. Cl.$^6$ ................................ C12N 5/00; A61F 2/10
[52] U.S. Cl. .......................... 435/366; 435/325; 435/395; 435/397; 435/398; 424/93.7; 623/15
[58] Field of Search ..................... 435/240.2, 240.243, 435/325, 366, 395, 397, 398; 623/15; 530/356; 424/573, 93.7

[56] References Cited

U.S. PATENT DOCUMENTS

| | | | |
|---|---|---|---|
| 4,703,108 | 10/1987 | Silver et al. | 530/356 |
| 5,282,859 | 2/1994 | Eisenberg | 623/11 |

FOREIGN PATENT DOCUMENTS

| | | |
|---|---|---|
| 6141452 | 2/1986 | Japan . |

OTHER PUBLICATIONS

Guesdon, et al.; The Journal of Histochemistry and Cytochemistry, vol. 27, No. 8, pp. 1131–1139; 1979.

*Primary Examiner*—Blaine Lankford
*Attorney, Agent, or Firm*—Merchant, Gould, Smith, Edell, Welter & Schmidt

[57] ABSTRACT

A method and apparatus for forming a permanent, composite skin replacement consisting of an epidermal component and a porous, resorbable, biosynthetic laminated dermal membrane component for use in wound repair. The dermal membrane is formed in the apparatus, which permits regulation of variables affecting membrane structure. The dermal membrane may be modified to incorporate biologically active molecules to enhance wound repair and to reduce infection when the skin replacement is applied to a wound.

7 Claims, 11 Drawing Sheets

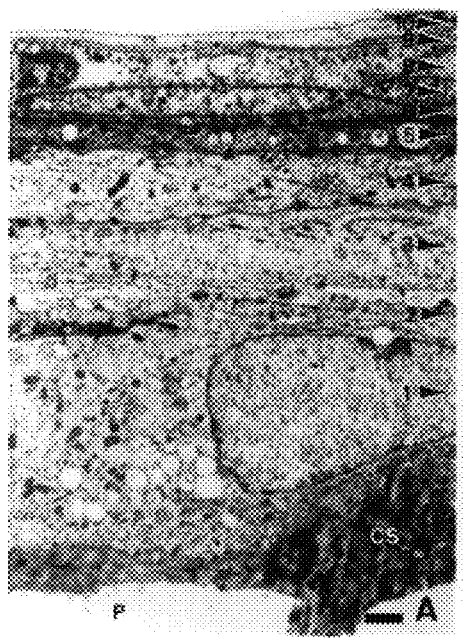
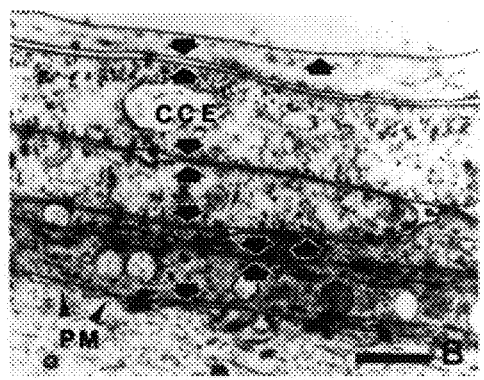
FIG. 4a   FIG. 4b
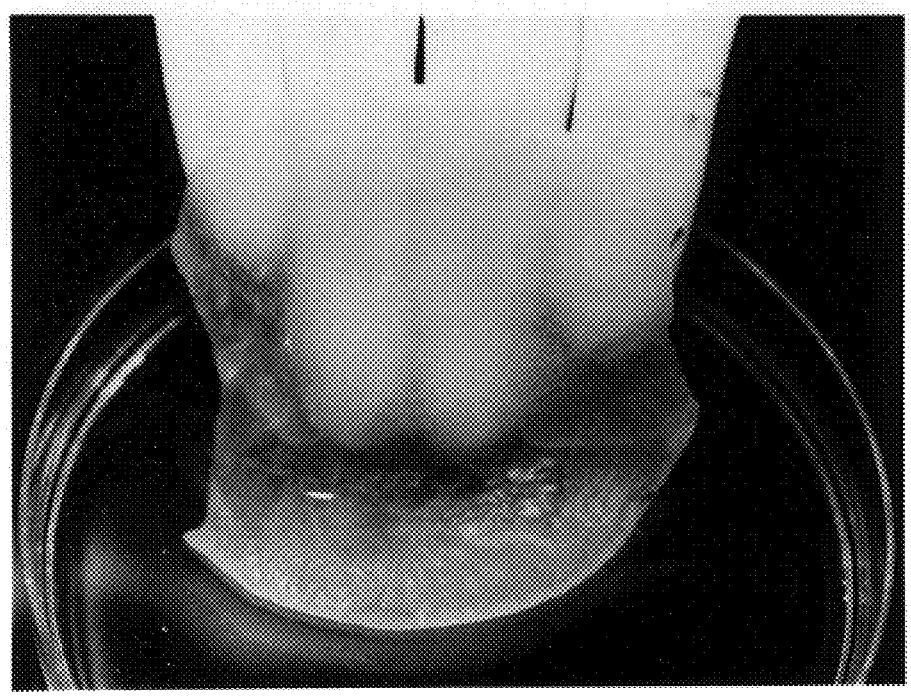
FIG. 2

& INSET

METHOD AND APPARATUS FOR PREPARING COMPOSITE SKIN REPLACEMENT

This is a continuation, of application Ser. No. 08/052,167 filed Apr. 23, 1993 now abandoned, which is a divisional of U.S. Ser. No. 759,641 filed Sep. 12, 1991, now U.S. Pat. No. 5,273,900 which is a continuation of U.S. Ser. No. 398,297, filed Aug. 24, 1989, now abandoned, which is a continuation of U.S. Ser. No. 186,603, filed Apr. 27, 1988, now abandoned, which is a continuation-in-part of U.S. Ser. No. 043,321, filed Apr. 28, 1987, now abandoned, contents of all of which are hereby incorporated by reference.

GOVERNMENT SUPPORT

This invention was made with government support under Grant No. GM-35068 with the National Institutes of Health. The Government has certain rights in this invention.

FIELD OF THE INVENTION

This invention relates to the field of materials suitable for use as a replacement of human skin, and more particularly to a method and apparatus for producing a composite skin replacement.

BACKGROUND OF THE INVENTION

Treatment of wounds, particularly burn wounds, requires early coverage of the wound to reduce fluid loss, pain, and infection by microorganisms. In addition, wound coverage facilitates repair of wounds which may involve restoration of both the epidermis and dermis. Burn wounds include partial thickness burns which destroy some, but not all of the epidermis and may destroy a portion but not all of the dermis. Most partial thickness burns will heal spontaneously if treated properly with synthetic dressings which can protect the wound and promote rapid epithelialization with minimal inflammation and scar formation. Full thickness burns destroy all of the epidermis and all of its adnexal structures (e.g. hair follicles, sweat glands and sebaceous glands) and usually all of the dermis. Full thickness burns may be treated initially by temporary coverage, but subsequently require grafting. Other wounds include donor sites which are the location from which undamaged (healthy) skin is removed for a skin graft. Parts of the epidermal adnexal structures remain in the donor site, regenerate the epidermis and heal the donor site spontaneously if the site is treated with appropriate dressings.

A successful skin graft requires that the graft accept onto debrided wounds (wounds from which the dead tissue or "eschar" has been removed) of the recipient to provide permanent re-establishment of he dermal and epidermal components of skin. The graft should not evoke an immune response which can destroy the graft and should provide or include a suitable dermal component to support the growth and development of a normal epidermis. The graft should suppress the formation of granulation tissue which causes scarring.

Treatment of wounds typically involves using skin grafts from ex vivo skin sources. Several types of skin grafts have been used to cover and/or repair damaged skin, for example in burn surgery. Autograits are the most effective skin grafts and are tissue transplants derived from the injured individual usually in the form of split-thickness skin grafts if used for permanent skin repair. A split-thickness skin graft consists of skin removed from a donor site and placed on a full thickness wound after debridment of the eschar to close and heal the wound. Split-thickness skin grafts consist of the epidermis, part, but not all of the eidermal adnexal structures and part of the dermis. Typically, a split-thickness skin graft is meshed (short alternating incisions) which allows for a maximum of 1:10 expansion of the graft tissue and usually an expansion of 1:3 or less. Other types of skin grafts include allografts which are tissue transplants between individuals of the same species but different genotypes, and homografts which are allografts from humans. Xenografts are tissue transplants between individuals of different species. Homografts of skin may come from live donors or from skin preserved in skin banks.

Permanent repair of excised full thickness and/or partial thickness burns ultimately requires restoration of stable tissue as a protective covering on the exterior of the body. Ideally, the repaired tissue duplicates the structure and functions of undamaged skin, including compartmentalization into normally organized epidermal and dermal components. Meshed split-thickness autograft meets these criteria, but is often unavailable in sufficient amounts for large body surface area (BSA) burns. In addition, contemporary procedures for surgical application of meshed autograft also inflict further injuries to patients and ordinarily accomplish ratios of tissue expansion that are less than 10 -fold the size of the donated tissue. These limitations in the use of meshed autograft for treatment of large BSA burns result in repeated surgical operations, protracted hospitalization, and undesirable cosmetic results. Thus, skin replacement after large BSA burns remains an unsolved problem.

Factors involved in graft success include characteristics of both the graft and the wound. Unmeshed split-thickness autograft provides the highest probability of acceptance and persistence of the wound, in addition to the high quality of repair for skin loss injuries including excised full thickness burns, achieved by such grafts. However, even an optimal graft of this kind may be only partially accepted on a suboptimal woundbed depending, for example, on the depth of exci sion, type of tissue in the woundbed and presence of infection.

Similarly, differences in graft acceptance may be expected depending on the composition of the graft applied to an optimal woundbed. In comparison to split-thickness autograft, biological materials such as fresh or frozen allograft dermis, fresh or processed porcine xenograft, collagen-based dermal implants and cultured human keratinocyte (HK) cell sheets, may be expected to be accepted onto wounds, in part, according to their respective capabilities to support ingrowth of the fibrovascular tissue (connective tissue and blood vessels). Cultured HK cell sheets, due to the intrinsic lack of vascular supply in the epidermis, may be expected to be accepted onto wounds corresponding predominately to the degree and quality of vascularized connective tissue in the woundbed. Acceptance of 60 to 80% of HK cell sheets onto beds of granulation tissue after allograft removal has been reported (Gallico et al, *New Eng. J. Med.*, 311(7):448–451 (1984)) but the acceptance of cultured HK grafts onto freshly excised full thickness burns has met with little success. Furthermore, although granulation tissue may serve as a satisfactory woundbed for acceptance of cultured HK and other grafts, it is also associated with the formation of scar tissue.

Disadvantages of skin grafts other than autografts include infection and frequent rejection by the recipient requiring the use of immunosuppressive agents. Research efforts have been directed towards developing functional synthetic substitutes that overcome the disadvantages of skin substitutes composed of animal skin to provide permanent wound closure.

Criteria for synthetic skin substitutes include: rapid adherence to the burn wound soon after placement; proper vapor transmission to control evaporative fluid loss from the wound and to avoid the collecion of fluid between the wound and the dressing material. Skin substitutes should also be flexible, durable and resistant to tearing and should act as a barrier to microorganisms, as well as limit the growth of microorganisms already present in the wound. The substitutes should exhibit tissue compatibility, i.e. not provoke inflammation or foreign body reaction in the wound which may lead to the formation of granulation tissue. An inner surface structure should be provided that permits ingrowth of fibro-vascular tissue. Hansbrough, (speaker), *J. of Trauma* 24:S31–S35 (1984).

A variety of materials that are obtained from either in vitro or ex vivo preparations have been proposed. These preparations may be grouped into temporary skin substitutes, i.e. requiring subsequent autografting, and permanent skin substitutes. Temporary skin substitutes generally consist of those formed from biological materials, for example allografts and xenografts, and those substitutes formed from materials such as synthetic polymers. Permanent skin substitutes for full thickness wounds include autografts and dermal-epidermal composites. For partial skin substitutes dermal replacements such as collagen-based implants or epidermal substitutes, for example sheets of human epidermal cells, have been investigated as permanent skin substitutes.

The use of synthetic polymeric materials in various forms has been promising for the development of skin structures having the ability to induce cellular migration and proliferation into the graft, but has been limited by the high incidence of infection and inability to promote vascularization and epithelialization. Epithelialization of the membrane graft provides a barrier to infection and contributes to the control of fluid loss. In addition polymeric materials may fail to adhere to the wound or to control infection.

Various materials have been demonstrated to function as full (epidermal and dermal) or partial (epidermal or dermal) permanent substitutes for meshed split-thickness autograft. The use of tissue culture techniques for normal HK can accomplish expansion ratios (the ratio of the original size of the donor skin to the area of cultured cells at the time of grafting) that can exceed 1000-fold of the original size in a period of from 3 to 4 weeks. Boyce and Ham, *J. Tiss. Cult. Meth.* 9(2):83–93(1985); *J. Invest. Dermatol.* 81(1), Supp. 335–405 (1983). HK cultures of these kinds will form multilayered sheets and have been shown to provide wound closure after application to excised full thickness burns as sheets on top of allogeneic dermis. Cuono et. al., *The Lancet* 1:1123–1124(1986). The high expansion ratios of HK and their ability to form sheets contribute to both the predictability and rate of graft acceptance onto wounds. Some full permanent skin substitutes are applied in two stages with de-epidermized allograft applied first to the woundbed followed either by autologous epidermal suction blisters (Heck et. al., *J. Trauma* 25(2):106–112 (1985)) or by autologous HK cultures (Cuono et. al., supra). Although such approaches may offer distinct advantages over meshed split-thickness autografting, they remain subject to availability and variability of human allograft. Furthermore, these kinds of approaches require two events of graft acceptance to complete wound closure, whereas split thickness autograft requires only one.

The desirability of using biological materials has led to the development of skin substitutes using collagen, which is a major component of normal connective tissue. However, the use of collagen alone, for example as a reconstituted collagen film or sheet, has not been demonstrated to serve as an effective wound covering because it stimulates the development of granulation tissue and elicits a chronic inflammatory response before being resorbed (biodegraded). In addition, collagen in the form of sheets is inelastic and fails to control the growth of microorganisms in the wound. Work with collagen-based sponges as wound dressings indicates that structural characteristics of the sponge such as pore size and fibrous structure may be affected by regulation of freezing temperature, viscosity and pH of the collagen dispersion used to form the sponge. Doillon et al, *J. Biomed. Materials Res.*, 20: 1219–1228 (1986).

Dermal-epidermal composites are a useful alternative for wound coverings. These materials generally consist of two components; a component for adherence to the wound, with a semi-permeable membrane as the exterior component. Examples include the material Biobrane® (Tavis et al, *Burns*, 7:123–130 (1981)) as a temporary wound covering. Biobrane® consists of a knitted nylon mesh covered with a thin silicone membrane, with the layers bonded with collagen peptides.

Permanent dermal skin replacement has been demonstrated using resorbable synthetic composites consisting of collacen and chondroitin-6-sulfate (glycosaminoglycan (GAG)) dermal membranes as described by Burke et al, *Ann. Surg.* 194(4):413–428 (1981); Yannas et al, *Science* 214:174–176 (1982), Yannas et al, U.S. Pat. No. 4,060,081; and Boyce et al, Program of the Amer. Burn Assoc., 18th Ann. Meeting, Abst. No. 30 (1986). In addition, allogeneic dermis (Cuono et al, supra, and Heck et al, supra) and fibroblast-collagen-gel mixtures (Bell et al, *J. Invest. Dermatol.* 81(1), supplement:2s–10s(1983)) have been used. Unfortunately, allogeneic dermis may be difficult to obtain in large quantities and may serve to transmit disease between the donor and the reciient. Fibroblast mixtures are unstable over lone periods of storace and may be excessively thick for use as certain grafts, such as split-thickness skin grafts.

The composite membrane described by Yannas et al. in U.S. Pat. No. 4,060,081 consisting of a dermal layer of collagen and a mucopolysaccharide such as chondroitin-6-sulfate (a glycosaminoglycan (GAG)) is covered with a Silastic® (medical grade silicone rubber) "epidermal" component. While this skin substitute is biodegradable and is not inflammatory or immunogenic, it requires that the Silastic® epidermis be removed at a later date and that the dermal layer be covered with a thin autograft to provide the epidermal component for permanent wound closure. The material is also limited by premature loss of the Silastic® layer leading to damage of the neodermis formed by vascularization of the collagen framework. This may be followed by development of granulation tissue which leads to scarring and undesirable functional and cosmetic results.

Imoroved methods for culturing epidermal cells such as HK have been developed and attempts have been made to grow the cells on artificial membranes such as that developed by Yannas et al, supra. In particular, improvements have been made in culture media, for example using the culture medium MCDB 153 described by Boyce and Ham, in In Vitro Models for Cancer Research, Vol. II (Eds. Webber and Sekely, Boca Raton, CRC Press, p. 245–274 (1986); *J. Tiss. Cult. Meth.* 9(2): 83–93 (1985); and *J. Invest. Dermatol.* 81(1) supplement: 33s–40s (1983)). More recently, this medium has been further modified to contain elevated amounts of selected amino acids. Pittelkow et al, *Mayo Clin. Proc.* 61: 771–777 (1986).

Although prior attempts have achieved growth of the cells on an artificial membrane, certain problems remain unsolved. For example, when HK cells are inoculated on the collagen-GAG membrane described by Yannas et al., the cells tend to migrate down into the interstices of the membrane which results in a material that is not structurally compartmentalized into epidermal and dermal components in the manner of normal skin.

There is a continuing need for a composite skin replacement for permanent wound coverage and repair which provides discrete epidermal and dermal components, promotes wound healing and reduces infection and which optimizes fibro-vascular invasion from the wound bed into the dermal component. In addition, efficient and inexpensive methods for manufacturing such composites are needed.

SUMMARY OF THE INVENTION

Accordingly, the invention provides material and a method and apparatus for its preparation which is permanent, composite skin replacement consisting of human epidermal cells such as keratinocytes, in combination with a biosynthetic, acellular dermal membrane component which may be formed using collagen and mucopolysaccharide. The dermal membrane component is formed using the apparatus of the invention and may be surface-laminated for localization of the epidermal cells to the surface of the membrane component. The method includes tissue culture of the epidermal cells, and preparation of the dermal membrane using the apparatus which allows regulation of the formation of the membrane to optimize porosity and thickness for vascular ingrowth. The cultured epidermal cells attach to the dermal membrane in vitro forming the composite skin replacement. The surface-laminated dermal membrane component of the composite skin replacement maintains discrete dermal and epidermal compartments, and may be grafted onto wounds in a single application. The dermal component may incorporate biologically active molecules such as growth factors to enhance wound repair. Biologically specific compounds such as avidin or biotin covalently bound to the biologically active molecules are reacted with the biotinylated dermal component to incorporate the active molecules into the dermal component. The so-modified dermal component is then combined with the epidermal cells to form the composite skin replacement of the invention.

BRIEF DESCRIPTION OF THE DRAWINGS

The details or typical embodiments of the present invention will be described in connection with accompanying drawings in which:

FIG. 2 is a photograph of a composite skin replacement prepared according to the method of the invention.

FIG. 3A depicts composite skin replacement after 5 days incubation in culture medium containing 20% (v/v) FBS, FIG. 3B depicts composite skin replacement after 5 days incubation in serum-free culture medium, FIGS. 3C and 3D depict mitotic cells in composite grafts, and FIG. 3E depicts split thickness skin graft.

FIGS. 4A and 4B are transmission electron micrographs of a composite skin replacement after 11 days in culture, namely, FIG. 4A indicates bottom to top showing pores (P) in the collagen substrate (CS) with numbers on the right identifying 10 HK layers, and FIG. 4B indicates uppermost HK strata with cornified cell envelopes (CCE), and uncornified plasma membrane (PM), scale bars=10 µm cell envelopes (CCE), and uncornified plasma membrane (PM), scale bars=10 µm.

DETAILED DESCRIPTION OF THE INVENTION

Figure 1A:
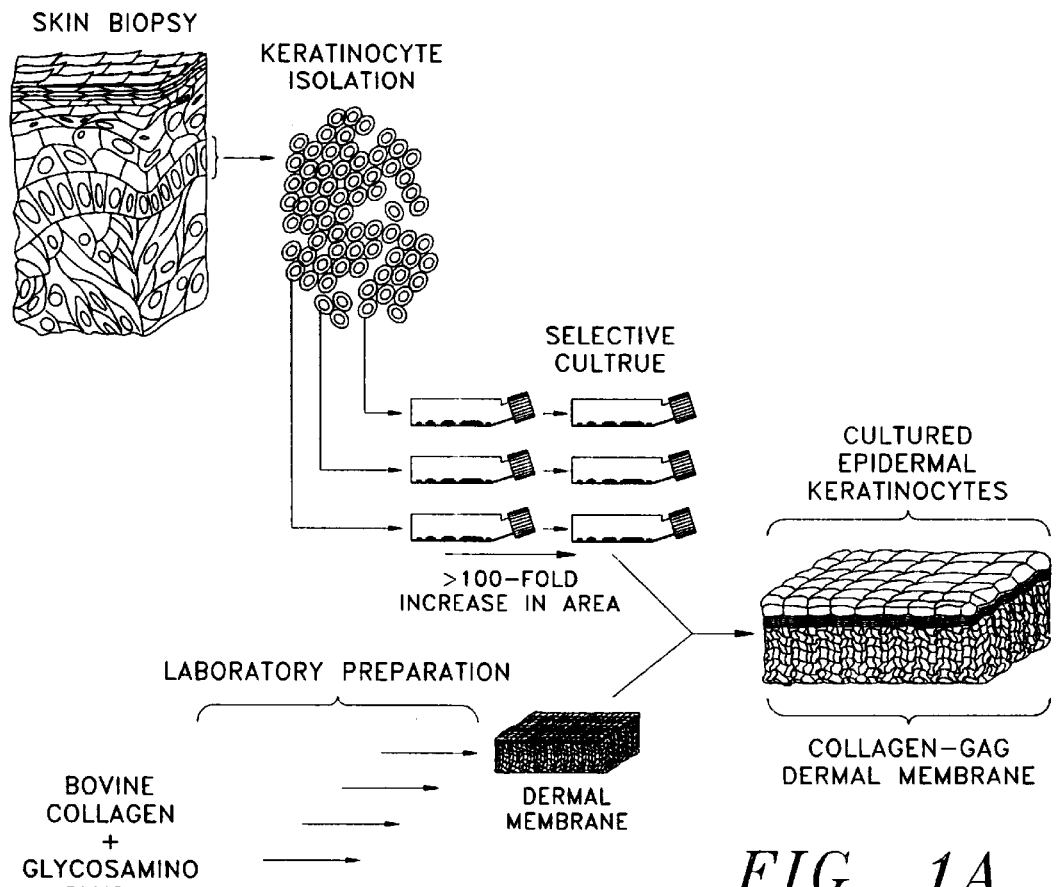
FIG. 1A is a diagrammatic representation of the method used to prepare the composite skin replacement.
Figure 1B:
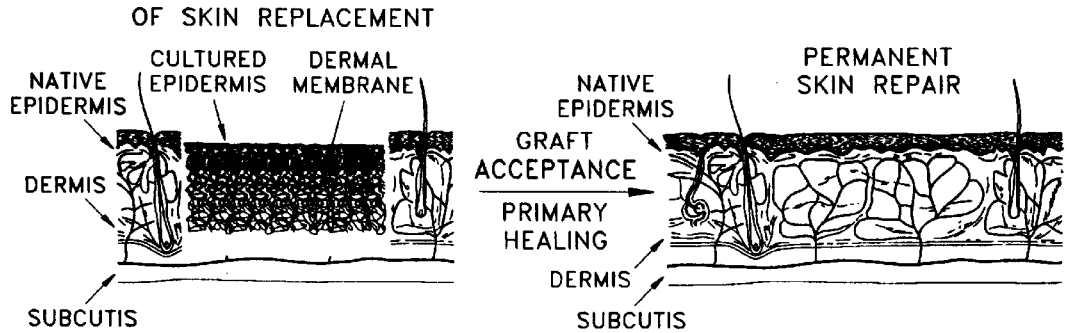
FIG. 1B depicts grafting of the skin replacement onto a wound.

The present invention includes a method for preparing a permanent composite skin replacement consisting of a biological epidermal component and an acellular, biosynthetic (biological material prepared by synthetic procedures), porous, resorbable dermal membrane component. Preferably, the epidermal component includes cultured human epithelial cells such as normal human keratinocytes (HK) which are cultured on the dermal membrane and attach to the membrane to allow subsequent grafting of the composite formed to a wound. For use in the composite, the epidermal cells may be derived from epidermal tissue which is genetically identical to the tissue of the composite recipient (autogeneic cells) or may be derived from isospecific (same species) but genetically dissimilar (allogeneic) tissue.

The dermal membrane component may be prepared using the apparatus of the invention. The dermal membrane is preferably prepared from collagen, for example bovine collagen and a mucopolysaccharide, for example a glycosaminoglycan (GAG) such as chondroitin-6-sulfate. To maintain the composite skin replacement in a compartmentalized form similar to human skin, the dermal membrane is preferably surface-laminated using a biopolymeric material, for example a layer of a solution containing collagen and GAG.

According to the method of the invention, proliferating normal human epidermal cells, preferably keratinocytes, are expanded exponentially in number to increase the area of the dermal membrane covered by the cultured HK, compared to the area of skin tissue from which the HK culture is originally established. This expansion may exceed up to 1000-fold the area of epithelial tissue from which the cells were isolated. The cells are cultured under optimal conditions which include using a growth permissive culture medium such as MCDB 153 containing elevated amounts of selected amino acids, epidermal growth factor, insulin, hydrocortisone, ethanolamine and phosphoethanolamine and lacking transferrin and progestrone, as described by Boyce and Ham, supra, and Pittelkow et al, supra, all of which are incorporated by reference herein. The cells are cultured until the expansion ratio exceeds 10-fold, after which a portion of the cells are transferred to dermal membranes. The remainder of the cells are allowed to continue to grow and are subsequently transferred to dermal membranes before transplantation of the composite to damaged skin.

The membrane solution is frozen, preferably in the freezing chamber of the membrane-forming apparatus of the invention described below under carefully regulated temperature conditions, then is lyophilized (freeze-dried), and cross-linked by physical or chemical means. The surface of the dry membrane formed may be laminated with an additional layer of biopolymeric material such as a solution of collagen and GAG containing a volatile cryoprotectant, for example dimethyl sulfoxide (DMSO). The laminating layer restricts the epidermal cells that are subsequently cultured on the membrane to the surface of the composite, and prevents cells from migrating into the interior of the porous membrane. After lamination, dry membranes are rehydrated, physically cross-linked, for example using high temperatures and a vacuum, or ultraviolet light, or chemically cross-linked with glutaraldehyde. The cross-linked membranes are then thoroughly washed and stored.

Dermal membranes exhibiting optimal porosity and thickness for fibro-vascular ingrowth may be prepared by placing the membrane solution described above in the membrane-forming apparatus of the invention.

Figure 8:
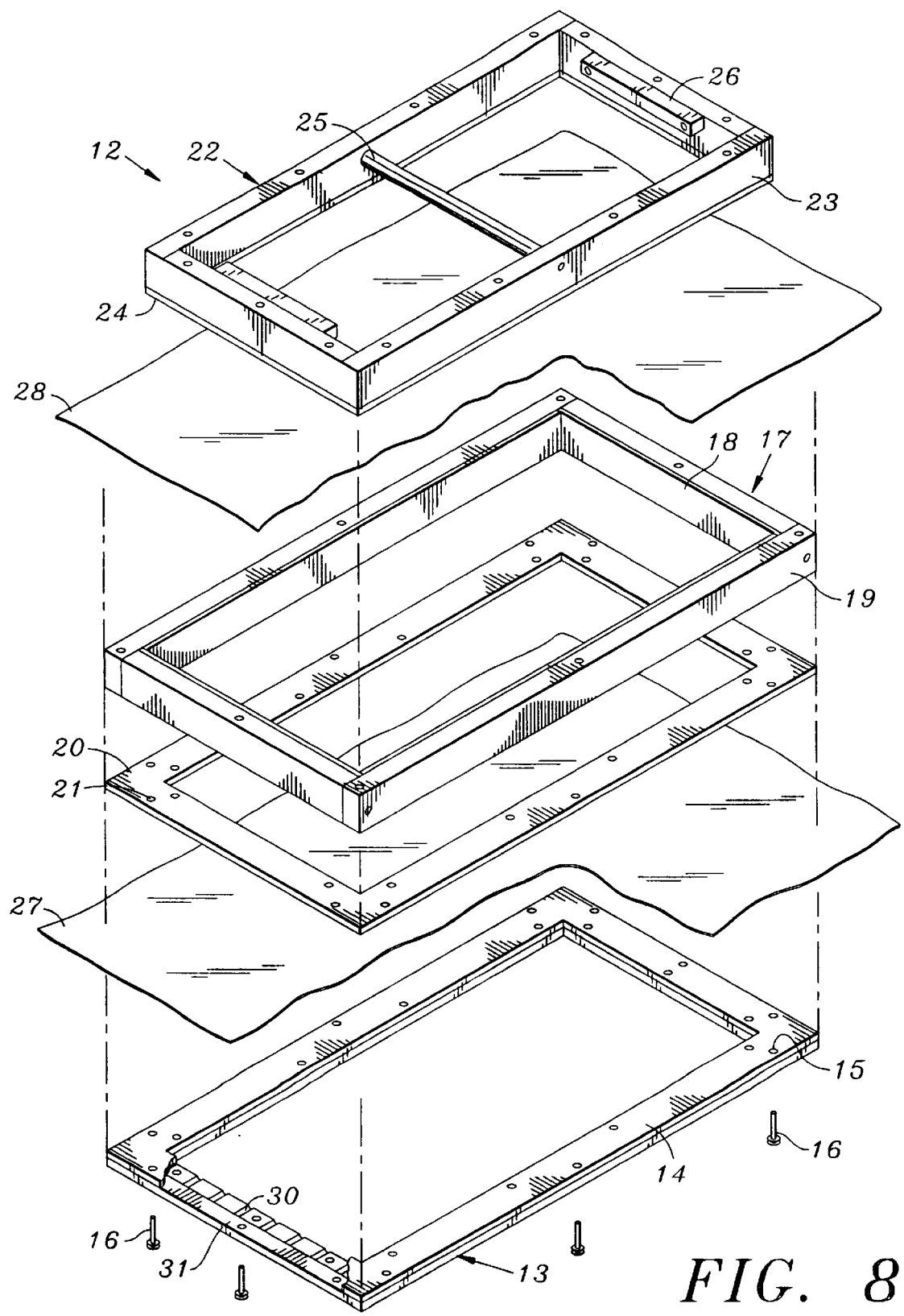
FIG. 8 is an exploded isometric view of the apparatus for preparing the dermal membrane of the invention.
Figure 9:
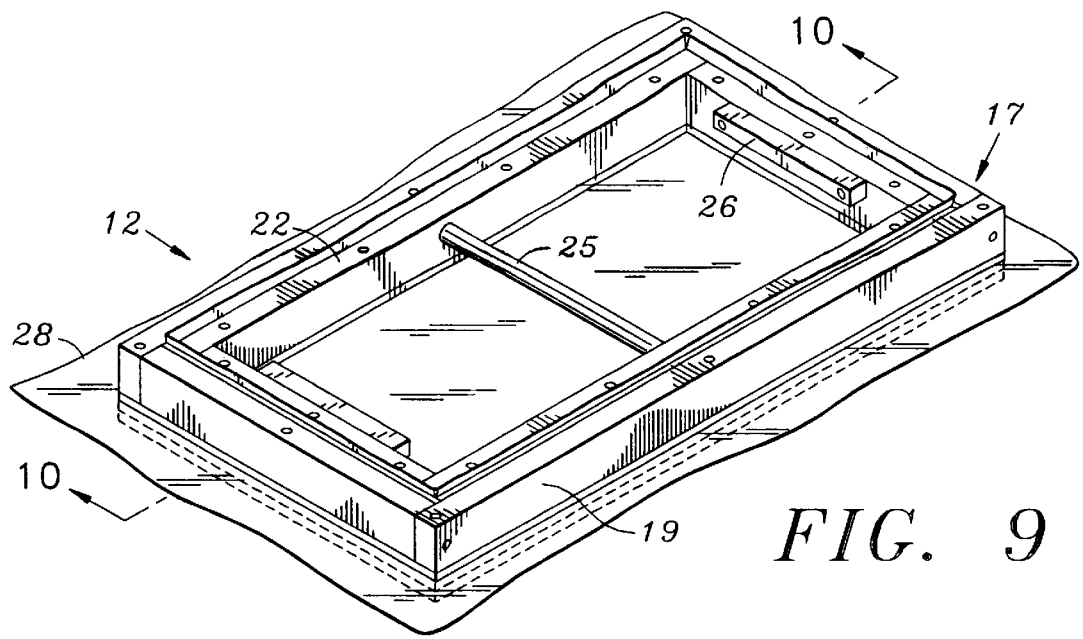
FIG. 9 is an isometric view of the assembled apparatus.

As shown in FIGS. 8–11, the apparatus 12 consists of three frames which may be of rectangular shape; a bottom frame 13 which may be constructed of aluminum or steel or other inflexible material such as wood or hard plastic, and which has a resilient gasket 14 which may be silicone rubber or other synthetic material, affixed to its upper surface. Bottom frame 13 has holes 15 for receiving assembly screws 16. An outer frame 17 constructed of material similar to the bottom frame 13 is lined with a resilient gasket 18 made of silicone rubber or other synthetic material. The outer frame 17 has walls 19 which extend vertically upward, and also has holes (not shown) for receiving assembly screws 16. A spacer gasket 20 constructed of silicone rubber or other synthetic material is inserted during use between the bottom frame 13 and the outer frame 17, and protrudes into the center of the apparatus as shown clearly in FIG. 10 and 11. Spacer gasket 20 also has holes 21 for receiving assembly screws 16. An inner frame 22 has internal dimensions which allow it to fit snugly within the outer frame 17, and may have vertical walls 23 which taper inward from top to bottom to facilitate insertion into the outer frame 17. The inner frame 22 also has a resilient gasket 24 affixed to its lower surface. In addition, the inner frame may be provided with a cross bar 25 to reduce flexure of the sides of the inner frame and handles 26 for removing the inner frame from the outer frame. Sheets of flexible, non-stick material, such as teflon (polytetrafluorethylene) are preferably used with the apparatus. A lower sheet 27 is inserted during assembly of the apparatus between the bottom frame 13 and the spacer gasket 20 and an upper sheet 28 is inserted between the outer frame 17 and the inner frame 22 as shown in FIG. 8.

Figure 10:
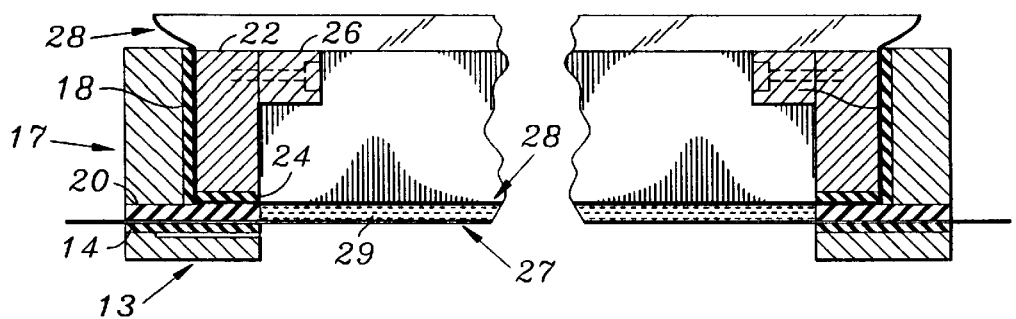
FIG. 10 is a section view taken along line 10—10 of FIG. 9.

As shown in FIG. 10, the assembled apparatus provides a freezing chamber 29 bounded on the upper and lower sides by the lower 27 and upper 28 teflon sheets and on the perimeter by the spacer gasket 20 for containing the membrane solution (indicated by hatched lines in the chamber 29 in FIG. 10) during freezing. The bottom frame 13 may be equipped with ducts 30 which are connected to a channel 31. (FIG. 8). Air bubbles which form in the freezing bath, under the lower teflon sheet 27, may be removed via the ducts, for example using a syringe inserted into the channel 31 to apply suction.

Figure 11:
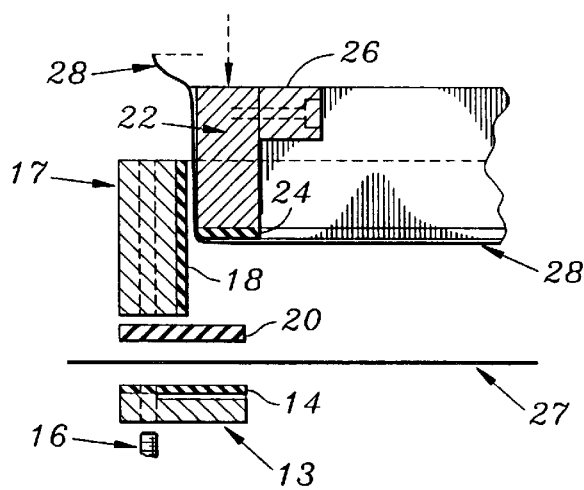
FIG. 11 is a partial-exploded section view taken along line 10—10 of FIG. 9.

Referring to FIGS. 6, 9, 10 and 11, to assemble the apparatus 12 the lower teflon sheet 27, is placed on the resilient gasket 14 of the bottom frame 13. The spacer gasket 20 is then placed on top of the lower sheet 27. Next, the outer frame 17 is placed on top of the spacer gasket 20 and screws 16 are inserted into the holes 15 in the bottom frame 13 then through the lower sheet 27, into the holes 21 in the spacer gasket 20 and into holes (not shown) in the outer frame 17, so that a portion of the spacer gasket 20 extends beyond the inner edge of the outer frame 17 into the freezing chamber 29. (FIGS. 10 and 11). The upper teflon sheet 28 is placed over the outer frame 17. The inner frame 22 is then snugly fitted into he outer frame 17 by pressing down so that the upper teflon sheet 28 folds up around the inner frame 22 and between the inner 22 and outer frame 17 as shown in FIGS. 10 and 11. The outer edges of the inner frame 22 contact the resilient casket lining 18 of the outer frame 17 when the inner frame is within the outer frame, and form a seal. The spacer gasket 20 does not protrude beyond the edge of the inner frame 22 when the apparatus is assembled.

The apparatus may be used to form a membrane with predetermined structure as follows. A suitable membrane solution, for example a solution containing collagen and GAG as described above for forming synthetic dermal membrane, is poured onto the lower teflon sheet 27 and the protruding portion of the spacer gasket that forms the perimeter of the freezing chamber 29. The upper sheet 28 is then placed over the solution and outer frame. The inner frame 22 is then pressed into the outer frame 17. The membrane solution is thus located in the freezing chamber 29 formed between the two teflon sheets 27 and 28 and the spacer gasket 20. (FIG. 10). The dimensions of the freezing chamber 29, occupied by the solution, are determined by the thickness of the spacer gasket 20, which may be fabricated in a range of thicknesses for this purpose. These dimensions define the volume of membrane solution which may be placed in the freezing chamber 29.

The membrane solution may be frozen in the apparatus as follows. After the solution is poured into the freezing chamber 29 between the teflon sheets 27 and 28, the apparatus 12 is placed into a freezing bath, for example a shallow pan containing isopropanol at a selected temperature. Preferably, the freezing bath is deep enough to contact the lower teflon sheet and has sufficient volume and specific heat to absorb heat from the membrane solution at an optimal freezing rate. The isopropanol is also poured onto the upper teflon sheet, immediately after placing the lower teflon sheet in contact with the freezing bath to provide a uniform rate of freezing. Bubbles of air which may form under the lower teflon sheet may be removed by suction from the channel 31 connecting the ducts 30, as depicted in FIG. 8. Other methods of freezing the membrane solution within the freezing chamber may be used, for example contacting the chamber with acetone cooled with dry ice or with liquified gases such as nitrogen, propane or air. The inner frame 22 and the upper sheet 28 are removed before lyophilization. The frozen membrane is then lyophilized in a standard freeze-drying device in which the temperature is carefully monitored and regulated, for example using a digital temperature controller and temperature probe. The lyophilized membrane is then thermally dehydrated (in an oven using a vacuum) to physically crosslink the GAG to the collagen, and the individual compounds to one another. Dry membranes are removed from the apparatus before further treatment. Once dried the membrane may be stored or further treated.

Lamination of the surface of a dermal membrane formed as described above promotes localization of epidermal cells at the surface of the membrane, rather than penetration into the membrane. Lamination of the surface of the dermal membrane may be accomplished by coating or spraying a solution of biopolymeric materials and a volatile cryoprotectant such as dimethyl sulfoxide (DMSO) onto a non-stick surface, for example a teflon sheet. A useful laminating composition may be prepared from collagen, GAG and DMSO. The DMSO may be used at concentrations ranging from about 0.1 to about 10% and preferably at about 3%. When the application of the laminating composition to the teflon surface is complete, a dermal membrane prepared as described above, is placed on the sprayed surface in contact with the laminating composition. The teflon is then placed on a chilled metal surface, such as a brass plate that has been cooled with liquid nitrogen, and the membrane and laminating layer is allowed to freeze. The laminated membrane is then lyophilized, dehydrated under heat and vacuum and may be stored in the dry state. Prior to tissue culturing, laminated membranes are rehydrated, for example in 0.05 M acetic acid, then washed exhaustively with water and then with a suitable culture medium.

The dermal component of the skin replacement of the present invention may be modified to incorporate biologically active molecules such as growth factors, for example to enhance he wound healing abilities of the skin replacement and/or to reduce wound infection.

Figure 12:
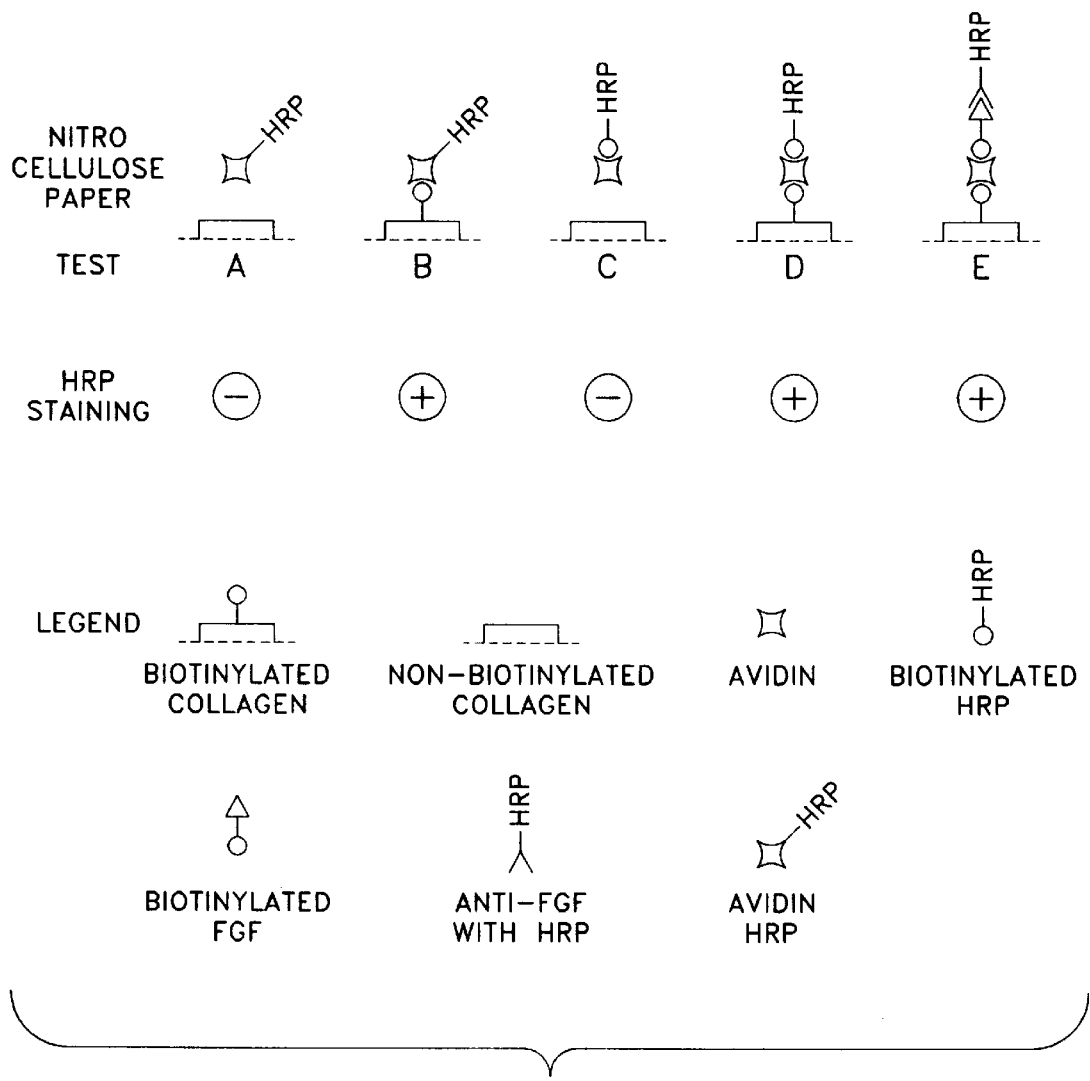
FIG. 12 is a schematic diagram depicting the various methods for attaching biologically active compounds to a substrate as described in Examples V and VI, infra.

Incorporation of biologically active molecules is achieved by integration of two biochemical mechanisms, covalent binding and conjugation. FIG. 12 depicts the various mechanisms for incorporating active molecules into the skin replacement of the present invention. "Covalent" binding is formation of non-ionic chemical bonds by sharing of electrons between atoms of the molecule. Covalent bonds are diagrammed in FIG. 12 as short lines connecting molecules or molecules to substrate. "Conjugation" refers to the very high affinity association between molecules that is not chemically covalent association. Conjugation together of two or more molecules is diagrammed as close approximation of molecules or molecule to substrate in FIG. 12. Various biospecific attachment mechanisms may be used, such as antibody/antigen, or avidin/biotin pairs. For example, biotin may be covalently bound to a biopolymer of the dermal component of the skin replacement, such as collagen, so that the collagen becomes "biotinylated". The biotinylated collagen is then conjugated with a polyconjugal protein, avidin, which in turn has been covalently bound to a biologically active molecule such as a growth factor for example Epidermal Growth Factor, Fibroblast Growth Factor (FGF), Platelet-Derived Growth Factor, Insulin-like Growth Factor, Transforming Growth Factors ($\alpha$ and $\beta$), and other growth factors, hormone, antibiotic or anti-inflammatory compound. The avidin thus acts as an adhesive between the biotinylated compounds such as collagen and the biologically active molecule. In the following examples, biotin was bound to solubilized collagen for conjugation with avidin to incorporate specific quantities of biologically active molecules into the dermal membrane. In another binding mechanism, biotin may be covalently bound to biologically active molecules and conjugated to the biotinylated collagen by using avidin, as shown diagrammatically in FIG. 12E.

A composite skin replacement according to the invention may be produced by cultivating epidermal cells such as normal human epidermal keratinocytes in log phase growth in a growth permissive medium such as MCDB 153 modified as described above. The cells are inoculated at a sufficient density onto the surface-laminated dermal membranes prepared as described above and are incubated until the cells form a confluent epithelial layer or sheet attached to the dermal membrane.

Biological acceptance of a synthetic membrane into a wound depends in part on the ability of non-inflammatory connective tissue cells to invade the membrane from the woundbed. Thus, the structural and biochemical characteristics of the membrane must be reproducible and optimized to promote fibro-vascular invasion. The method of the present invention includes control of structural characteristics such as porosity and thickness of the dermal membrane component of a skin replacement composite by regulation of specific variables during the preparation of the membrane component of the composite. These variables include the temperature used to freeze the membrane solution, the volume of solution frozen, and the concentration (percent weight/volume (% wt/vol)) of the compounds used to form the membrane.

Membrane pore size results from the rate of ice crystal growth during the freezing process which is inversely proportional of the rate of freezing. The rate of freezing is inversely proportional to the freezing temperature, and directly proportional to the thermal conductivity and specific heat of any materials which contact the membrane solution during the freezing process, for example the teflon sheets of the apparatus. Therefore, external pore size and pore size variability may be regulated by the temperature of freezing of the compounds used to form the membrane. Pore size is inversely proportional to the concentration of compounds (directly proportional to the concentration of water) in the membrane solution and to the rate of freezing of the membrane solution.

The thickness of the membrane is directly proportional to the concentration of compounds in the solution used to form the membrane and is directly proportional to the thickness of the spacer casket used in the membrane-forming apparatus.

In the apparatus of the invention used to form a dermal membrane, the sealed freezing chamber allows regulation of several variables during the freezing of the membrane solution. These include the temperature, thermal conductivity of the freezing bath, the volume of solution frozen, the concentration to the compounds used to form the membrane, and the thermal conductivity and specific heat of the materials which contact she solution, i.e. the non-stick sheets of the apparatus. Control of the rate of freezing may be accomplished by promoting rapid heat transfer from the liquid membrane solution to the environment. Therefore, the apparatus preferably includes a freezing chamber which allows maximum heat transfer, for example by using non-stick materials with high thermal conductivity such as teflon sheets with selected characteristics (e.g. approximately 0.008 to 0.025 cm thick at $6 \times 10^{-4}$ cal.-cm./sec.-cm$^2$-° C. conductivity) to form the upper and lower surfaces of chamber. In addition, the thickness of the membrane formed is directly proportional to the thickness of the spacer gasket selected for use in the apparatus.

The effects of temperatures of freezing on pore size of the membranes prepared using the method and apparatus of this invention may be determined by measurement of scanning electron micrographs of the dry membranes. Preferred temperatures of the freezing bath are between 0° C. and −200° C., more preferably between −20° C. and −50° C. and most preferably between −40° C. and −50° C. These temperatures minimize average pore size and variability of pore size in the membrane. The concentrations of membrane-forming compounds i.e., collagen and mucopolysaccharides, may be varied to yield a combined % wt/vol concentration which decreases the average external pore size and increases the thickness of the membrane. Combined concentrations of about 0.10 to about 2.0% wt/vol membrane compounds may be used, while about 0.50 to about 1.80% wt/vol are preferred.

Functional dermal membranes were obtained using the method and apparatus of the invention by selecting a 1 mm thick silicone spacer gasket, 0.52% wt/vol collagen-GAG solution and a freezing temperature of −40° C.

The examples which follow demonstrate the biological attachment and growth in vitro of epidermal cell cultures on porous, resorbable collagen-GAG dermal membranes to form a composite skin replacement with advantages over prior biosynthetic skin substitutes. The composite skin replacements prepared as described herein provided superior graft adherence in vivo to wounds compared to HK cultures alone. The keratinocytes grew and stratified to form a continuous epithelial layer over the surface of the dermal membranes. The cultured epidermis may re-establish a continuous epidermal cover that could protect a wound permanently. The composites were compartmentalized histologically similarly to natural skin, with the HK restricted to the external surface of the porous dermal membrane by the laminated collagen-GAG layer. In addition to serving as a mechanical support for epidermal cell sheets, the dermal membrane also promoted the ingrowth of vasculature and non-inflammatory tissue from a wound as demonstrated using the mouse model. The resulting restoration of connective tissue and epidermis may fulfill the need for stable tissue to repair a wound. The method and apparatus of the invention meet the need for a reproducible method for preparing a functional, composite skin replacement containing synthetic dermal membranes.

It will be understood by a person skilled in the art to which the invention pertains that numerous variations may be made in the temperature of freezing, thickness of the spacer gasket (volume of the freezing chamber) and concentration of the compounds used to form the membrane, to achieve a dermal membrane with optimal structure and porosity for use in wound repair. Variation in the parameters used to form the dermal membrane has been investigated and the results of these studies are set forth in the examples which follow.

The following examples describe the preparation of composite skin replacements according to he method and apparatus of the invention. The examples are presented to demonstrate the present invention and to assist one of ordinary skill in making and using the same. The examples are not intended in any way to otherwise limit the scope of the disclosure or the protection granted by Letters Patent granted hereon.

EXAMPLE I

Regulation of the Final Dermal Membrane Structure

Preparation of Membranes

Dermal collagen-chondroitin-6-sulfate membranes were prepared for studying the effects of freezing temperature and concentration of membrane starting materials on membrane structure as follows 1.2 grams of comminuted bovine collagen (USDA) were partially solubilized in 215 ml of chilled (4° C.) 0.05 M acetic acid and homogenized for one hour. 35 ml of chilled 0.05 M acetic acid was added to 0.11 g of chondroitin-6-sulfate (Sigma Chemical Co., St. Louis, Mo.) then stirred. The chondroitin-6-sulfate was co-precipitated with the collagen by dropwise addition to the collagen in a chilled (4° C.) homogenizer, while homogenizing over approximately two hours time. When all of the chondroitin-6-sulfate was added, the mixture was homogenized further for approximately 5 minutes. Bubbles were removed from the collagen-chondroitin-6-sulfate mixture using a vacuum. The mixture contained a combined concentration of collagen and chondroitin-6-sulfate of 0.52% weight/volume.

The co-precipitate solution was formed into membranes using the apparatus of the invention, with a 1 mm spacer gasket. The membrane solution was poured into the freezing chamber of the apparatus (approximate volume of 80 ml) shown in FIGS. 8 through 11, and the entire apparatus was placed in a 70% isopropanol freezing bath in a Virtis Unitop 800 lyophiizer (Virtis Co., Gardiner, N.Y.) (used or freezing and subsequently lyophilization) at −40° C. for 60 minutes. Shelf temperature was closely regulated during freezing to within ±1° C. by a digital temperature controller, and was monitored using a metallic temperature probe frozen to each shelf. Temperature probes were calibrated to 0° C. with water containing melted ice.

After freezing, the inner frame and upper teflon sheet were removed to expose the frozen membrane solution for further treatment. The apparatus was then returned to the shelves of the lyophilizer for freeze-drying at 30° C. at $1 \times 10^{-4}$ torr overnight.

Lyophilization was conducted until the membranes were completely dry. After lyophilization the membrane was carefully lifted out of the freezing chamber and placed on aluminum foil. The dried membrane was then placed in a vacuum oven for cross-linking by thermal dehydration at 105° C. and $1 \times 10^{-4}$ torr, for 24 hours.

The dried membrane was surface-laminated as follows. A 8×8 cm square of dermal membrane formed as described above, was laminated using 2.4 ml of a mixture of 0.52% wt/vol collagen-chondroitin-6-sulfate and 3% vol/vol DMSO. The mixture (0.060 ml/cm$^2$) was sprayed evenly onto a mylar sheet which was then placed for 2–3 minutes on a brass plate chilled with liquid nitrogen. The mylar was then removed and placed on the chilled lyophilizer shelf (−40° C.) and lyophilized as set forth above. The membrane was carefully packaged in plastic and stored at room temperature.

Prior to tissue culturing of HK cells on the dermal membranes the membranes prepared as described above were rehydrated in 0.05 M acetic acid for 24 hours, then chemically fixed using 0.25% glutaraldehyde in 0.05 M acetic acid for 24 hours. The membrane was then rinsed three times in sterile distilled water and transferred to 70% isopropanol (room temperature) and refrigerated. The isopropanol was changed three more times with sterile water and three times with culture medium before inoculation with HK cells.

Effect of Freezing Temperature on Membrane Structure

The membrane solution prepared as described above was frozen in a freezing bath at temperatures ranging from −50° C. to −20° C. using the apparatus of the invention. The materials were frozen in the apparatus then dried in a vacuum oven (105° C., $1 \times 10^{-4}$ torr) for 24 hours. For determination of membrane pore size, scanning electron micrographs (40× and 200× magnification) from each of two dry membranes or each freezing temperature were prepared. Three linear measurements of pore size were made at perpendicular axes across the micrographs and average pore diameter was scored as the mean number of intersections per unit of length. Pore size was expressed for measurements on each axis as: mean pore diameter vs. freezing temperature.

Data collected from the linear measurements of pore diameter vs. freezing temperature are summarized in Table I.

TABLE I

Effects of Freezing Temperature on Pore Size

| Pore Diameter[1] | Freezing Temperature | | | |
|---|---|---|---|---|
| | −49° C. | −40° C. | 30° C. | −20° C. |
| X-Axis | 39 ± 3 | 52 ± 6 | 83 ± 10 | 84 ± 13 |
| Y-Axis | 47 ± 5 | 80 ± 19 | 148 ± 36 | 230 ± 105 |

[1]mean diameter ($\mu$m) + SEM.

Table I indicates that the porosity of the dermal membrane prepared from an aqueous co-precipitate of bovine collagen and GAG expressed as the mean pore diameter can be regulated by the temperature of freezing of the co-precipitate. The average pore diameter increased with an increase in the temperature of the freezing bath. Increased pore size occurred asymetrically suggesting that a vectorial process (e.g. ice crystal formation) caused the increase. Variability of pore size also increased as a function of increased freezing temoeratures before freeze-drying. Reduction of pore size variability to a minimum by strict regulation of the freezing temperature during synthesis of the dermal membrane may contribute to higher rates of biological acceptance of the membrane by wounds.

Effect of Concentration of Membrane Starting Materials on Membrane Structure

Dermal membranes were also obtained having controlled pore size and thickness as a function of the combined concentrations (% wt/vol) of the membrane starting materials. Ten membranes (two at each of five concentrations of starting materials) were prepared as described in Example I using 0.38, 0.67, 1.20, 2.15 and 3.72 grams of bovine collagen dispersed in 215 ml of 0.05 M acetic acid in a refrigerated (4° C.) homogenizer. The collagen dispersions were precipitated with 35 ml volumes of 0.05 M acetic acid containing 35, 56, 185, 189 or 326 mg of chondroitin-6-sulfate (GAG), respectively. The resulting co-precipitates had % wt/vol concentrations of 0.17, 0.29, 0.52, 0.94 and 1.62. Each co-precipitate was frozen in the apparatus of the invention in a freezing bath at −40° C., lyophilized and treated by thermal dehydration at 105° C. and $1 \times 10^{-4}$ torr for 24 hours. Three dry samples of each membrane were prepared for and examined by scanning electron microscopy for determination of the external pore size. To determine pore size, three linear measurements were made at perpendicular axes across the micrographs (magnification 100×) and average pore diameter was scored as the mean number of intersections per unit length. Two wet samples of each membrane were fixed in 2% glutaraldehyde, prepared for histology, sectioned perpendicular to the external surfaces, and mounted onto glass slides. The thickness of the membranes was measured on an inverted microscope. Data are shown in Table II and expressed as mean pore diameter vs. the combined concentrations of starting materials.

TABLE II

Effects of Concentration on Pore Size

| Pore Diameter[1] | Concentrations (% wt/vol) | | | | |
|---|---|---|---|---|---|
| | 0.17 | 0.29 | 0.52 | 0.94 | 1.62 |
| X-axis | 174 | 143 | 122 | 78 | 80 |
| (±SEM) | 10.3 | 3.8 | 4.9 | 2.7 | 3.6 |
| Y-axis | 452 | 313 | 189 | 185 | 113 |
| (±SEM) | 19.9 | 28.3 | 11.7 | 4.7 | 4.8 |

[1]Values are for mean diameter ($\mu$m) + SEM.

As shown by Table II minimal pore size was obtained using a concentration of 0.94 to 1.62% wt/vol.

Data collected from linear measurements of membrane thickness vs. concentration of starting materials are summarized in Table III.

TABLE III

Effects of Concentration on Membrane Thickness

| | Concentrations (% wt/vol) | | | | |
|---|---|---|---|---|---|
| | 0.17 | 0.29 | 0.52 | 0.94 | 1.62 |
| Thickness | 50 | 308 | 624 | 1583 | 2624 |
| (±SEM) | 22 | 17 | 29 | 143 | 302 |

Tables II and III show that an increase in the concentration of starting materials in a collagen and GAG dermal membrane caused a decrease in the average external pore size of the dry membrane and an increase in the thickness of the wet membrane. Optimal thickness was achieved at a concentration of 0.52% wt/vol.

The procedures for preparation of the dermal membrane described herein are highly reproducible, and thus can be regulated deliberately within narrow limits to generate dermal membranes with predictable characteristics of thickness and pore size.

EXAMPLE II

In Vivo Application of Composite Skin Replacement Formation of Dermal Membrane

A dermal collagen-chondroitin-6-sulfate membrane was prepared as described in Example I having 0.52% wt/vol combined concentration of collagen and chondroitin-6-sulfate, 1 mm spacer gasket and freezing bath at −40° C.

Tissue Culture Conditions

HK cultures were initiated from human surgical discard specimens and cultured in nutrient medium MCDB 153 containing 0.3 mM calcium, increased amounts of selected amino acids, 10 ng/ml epidermal growth factor (EGF), 5 $\mu$g/ml insulin, 0.5 $\mu$g/ml hydrocortisone, 0.1 mM ethanolamine, and 0.1 mM phosphoethanolamine, 0.5% (v/v) bovine pituitary extract (BPE) and penicillin-streptomycin-Fungizone as an antibiotic-antimycotic agent.

Inoculation of Dermal Membranes with HK

Figure 3A:
FIGS. 3A, 3B, 3C, 3D, and 3E are photomicrographs of composite skin replacements in vitro, and of split thickness skin, specifically.
Figure 3B:
Figures 3C, 3D:
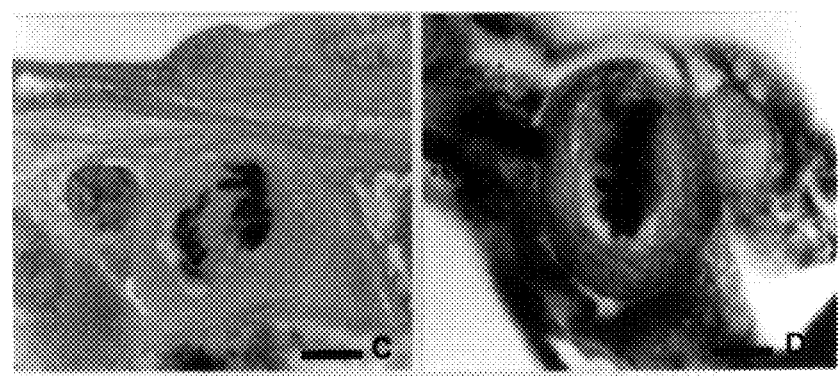
Figure 3E:

Dermal membranes 7 cm in diameter, were transferred sterilely from 70% isopropanol to petri dishes containing Hepes-buffered saline (3 changes) followed by tissue culture medium (2 changes, minimum of 1 hour each) as described or plus 20% (v/v) fetal bovine serum (FBS) (for grafting the composite to animals). Membranes were submerged in culture medium in a humidified incubator with 5% $CO_2$. HK in log phase growth were removed from flasks by trypsinization and inoculated onto the membranes at a density of 0.5 to $1.0 \times 10^5$ per $cm^2$. After 5–11 days incubation in the respective media with daily changes, the HK-dermal membrane composites were prepared for grafting or were fixed in buffered glutaraldehyde and prepared for microscopic examination. The composite had a total thickness of less than 0.5 mm (0.020 inches). The composites shown in FIGS. 3A and B ranged in thickness from 0.2 to 0.3 mm (0.008 to 0.012 inches).

Histology and Electron Microscopy

Dermal membrane-HK composites were embedded in glycol methacrylate (JB-4; Polysciences, Warrington, Pa) sectioned at 5 μm thickness and stained with 0.1% toluidine blue for light microscope histology. Identical specimens were embedded in Epon-Araldite (E. F. Fullam, Latham, N.Y.) followed by preparation of ultrathin sections, staining with uranyl acetate and lead citrate, and examination by transmission electron microscopy (TEM) as described by wolosewick et al, in Practical Tissue Culture Applications, (Eds. Maramorosch and Himur), Academic Press, N.Y., p. 58–85 (1979), incorporated by reference herein.

Physical qualities of composite skin replacement

Composites of cultured HK and collagen-chondroitin-6-sulfate membranes could be handled without secondary supports or transportation vehicles (FIG. 2). The replacements were draped into place, lifted and relocated without damage to the cultured epidermal surface, and were less fragile than cultured epidermal sheets alone.

The porous dermal collagen-chondroitin-6-sulfate membranes alone had limited elasticity and tensile strength as determined by subjective evaluation. After the formation of a partially stratified epidermal layer on the membrane's surface, the physical strength of the composite graft increased corresponding to the degree of stratification of the epidermal layer. Subsequent to the formation of an epidermal layer, in vitro, the composite graft had greater physical strength than cultured epidermal sheets alone or than the dermal membrane alone, but less than split thickness skin.

Hstology.

The histological appearance of the composite skin replacement was compared to split thickness skin as shown in FIG. 3. Five days after inoculation with cultured HK, a continuous and partially stratified epithelial layer had formed. The addition of 20% fetal bovine serum (FBS) for at least 48 hours promoted the formation of a uniform HK layer containing cuboidal cells attached to the membrane and flattened cells on the external surface (FIG. 3A). An identical sample without FBS (FIG. 3B) also exhibited cuboidal cells attached to the dermal membrane, but somewhat less well organized "suprabasal" HK layers. Histologies of both conditions showed discrete separation into epidermal and dermal compartments and mitotic cells adjacent to the dermal membrane (FIGS. 3C, D). The discrete dermal and epidermal compartments compared favorably to the histological organization of split thickness skin (FIG. 3E).

Transmission Electron Microscopy.

Figure 5:
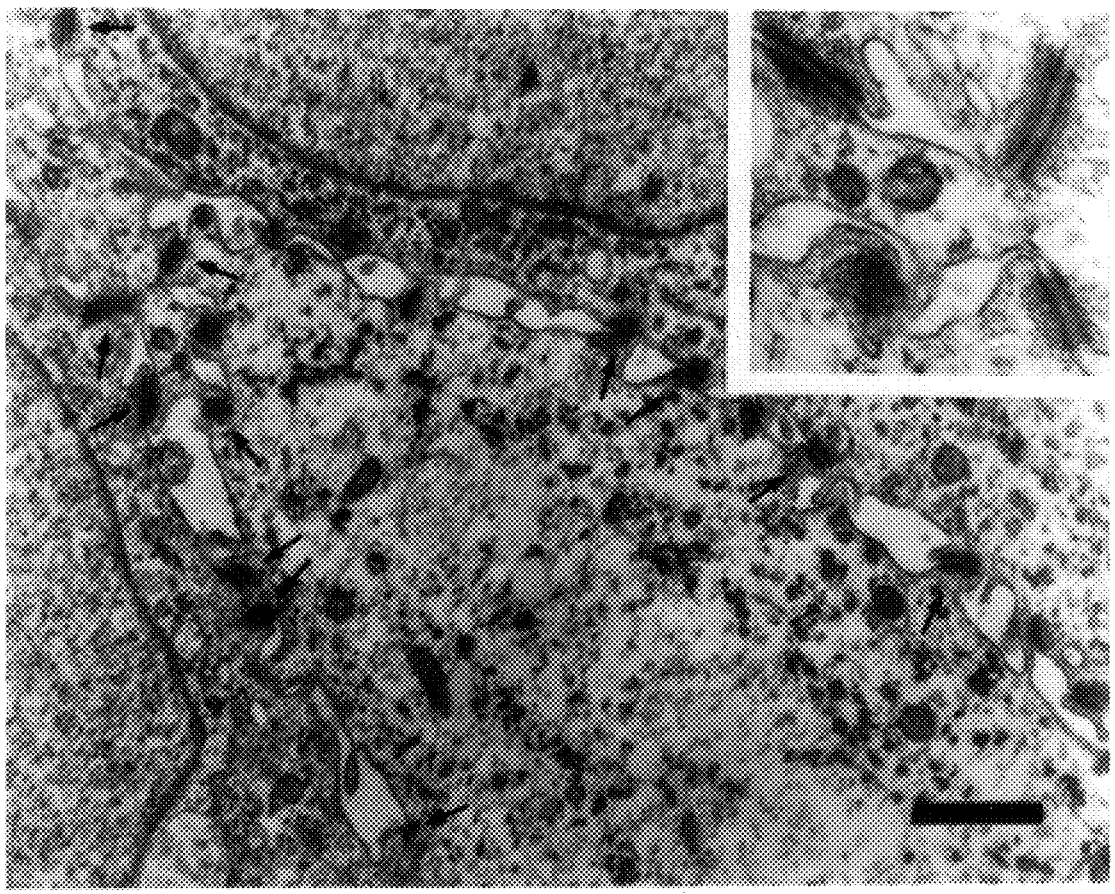
FIG. 5 shows transmission electron micrographs of desmosomes that interconnect HK cells in culture. Inset shows enlargement of desmosomal junctions between cells. Scale bar=10 µm.
Figure 6A:
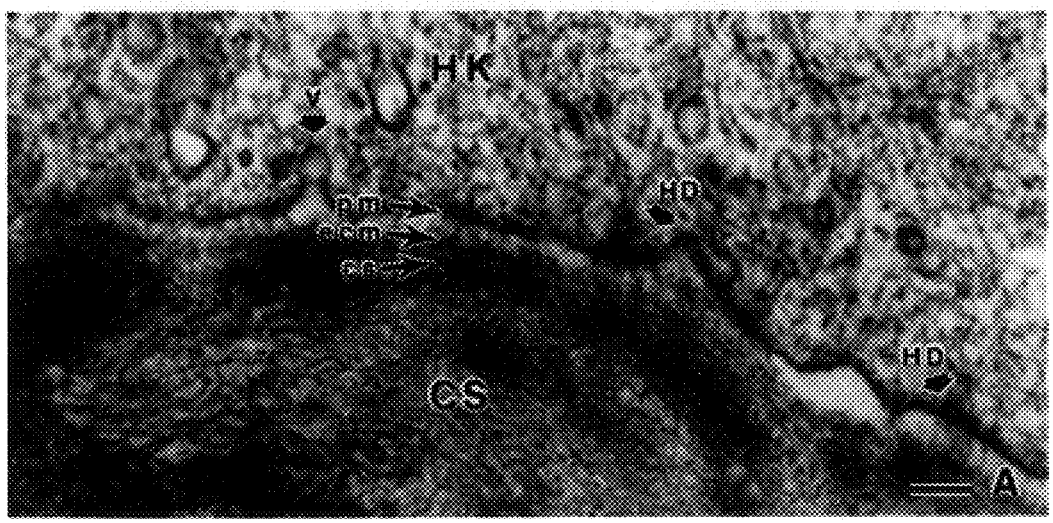
FIGS. 6A–6C are transmission electron micrographs showing biological attachments between HK cells and the collagen substrate, namely, FIG. 6A indicates HK cell attached to the CS by hemidesmosomes (HD) and formation of extracellular matrix (ecm), (v)=vesicles in the plasma membrane (pm), FIG. 6B indicates HD, pm and ecm, and FIG. 6C indicates arrows depicting banded collagen substrate, A, B; scale bars=1µ, C, scale bar=10 µm.
Figure 6B:
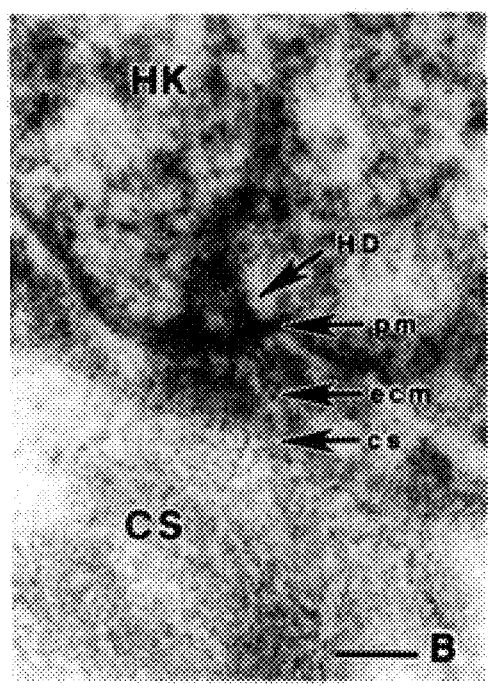
Figure 6C:
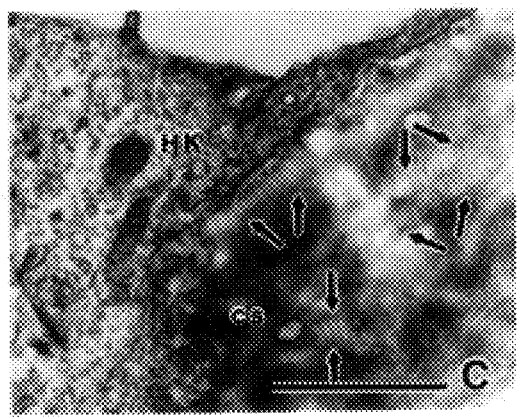

HK cultures on dermal membranes formed stratified, partially cornified epidermal layers after 11 days in culture (FIG. 4). At low magnification, 10 cell layers were seen (FIG. 4A). Cells attached to the dermal membrane were much less flattened than stratified cells not attached directly to the substrate. The uppermost strata only exhibit cornified cell envelopes (CCE, FIG. 4B). Desmosomes occurred frequently (FIG. 5) connecting the cell layers and confirming the epithelial nature of the cultured cells. At the interface of the cultured HK and the dermal membrane, cellular connections to the membrane were observed. Hemidesmosomes (HD) (FIGS. 6A, B) formed between HK cells and the dermal membrane to provide cellular adhesions to the substrate. Extracellular matrix (ECM; FIGS. 6A, B) was located continuously between HK and the membrane. The composition of the ECM was not determined, but HK cells grown in these culture conditions have been shown to deposit fibronectin on the substrate to which the cells attach. Kubo et al, J. Invest. Dermatol., 82(b): 80–586 (1984). HD and ECM were distributed uniformly along the cell-dermal membrane junction both in serum free samples and those with 20% FBS. In addition, composites exhibited extracellular fibers in the dermal membrane immediately adjacent to the cell-dermal membrane (FIG. 6C). The repeating pattern in the fibers is consistent with the periodic register of collagen. These fibers were only within very short distances of the cell-dermal membrane junction which implies their deposition by HK in culture.

Grafting to Animals

Athymic (nude) balb/c female mice were anesthetized with Avertin (tribromoethanol in tert-amyl alcohol) and full-thickness skin defects 2×2 cm were prepared to the level of the panniculus carnosis on the dorso-lateral aspect of the body immediately posterior to the forelimb.

Treatments administered to the defects included: A) 180° rotation and replacement of the excised skin (autograft), B) application of fresh human xenograft, C) application of the collagen and chondroitin-6-sulfate dermal skin replacement described above, and D) no graft. Following treatment, wounds were covered with Biobrane® that was attached to surrounding undamaged skin with occlusive, adhesive dressings (Op-Site®, Bioclusive®) and bandaged. After one week, animals that received the dermal skin replacement (C, above) were subsequently grafted with a combination of cell suspensions of actively growing human epidermal keratinocytes (HK) cultured as described above plus confluent sheets of HK and redressed. At day 41, animals were sacrificed, the repaired wounds were excised, photographed, and measured by computerized planimetry. Restoration of skin function after closure of full-thickness wounds with cultured skin. substitutes may be maximized, if wound contraction is minimized.

Data of wound contraction from the various treatments are shown in Table IV:

TABLE IV

| TREATMENT | % ORIGINAL WOUND SIZE | SEM | N |
| --- | --- | --- | --- |
| 1) Autograft | 37.65 | 6.29 | 5 |
| 2) Human Xenograft | 39.53 | 5.83 | 5 |
| 3) Composite Graft | 16.23 | 1.11 | 4 |
| 4) No Graft | 13.95 | 2.69 | 4 |

Results from a later experiment performed as described for the data in Table IV are shown in Table V.

TABLE V

| TREATMENT | % ORIGINAL WOUND SIZE | SEM | N |
|---|---|---|---|
| 1) Autograft | 67.50 | 2.73 | 11 |
| 2) Xenograft | 54.95 | 6.74 | 11 |
| 3) Composite Graft | 37.17 | 3.68 | 18 |
| 4) No Graft | 18.31 | 1.57 | 12 |

Figure 7:
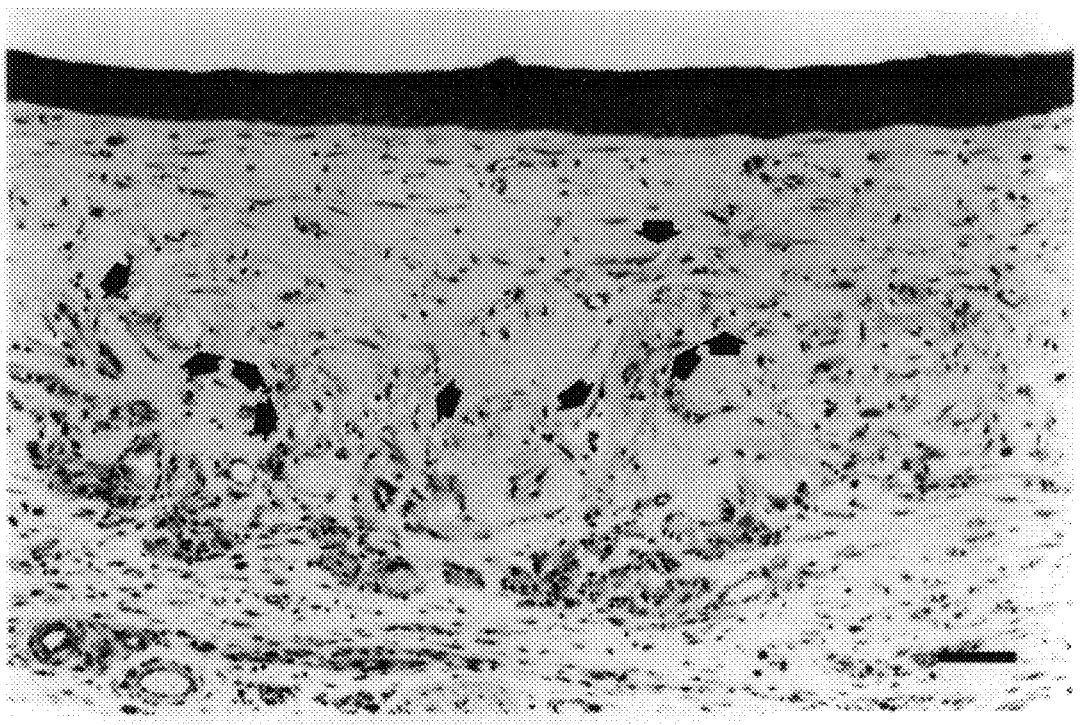
FIG. 7 is a photomicrograph of a full thickness skin defect treated six weeks before, using the composite skin replacement of the invention. Arrows indicate reticulated spaces formed by as yet non-resorbed dermal membrane. Scale bar=100 µm.

These results demonstrate that composite skin replacements consisting of collagen and chondroitin-sulfate dermal membrane and cultured human epidermal keratinocytes were less effective in reducing wound contraction that intact murine autograft or human xenograft, but more effective than no graft. The skin replacements may thus serve as a biological cover to delay contraction of open wounds temporarily. Skin repaired with the composite graft resembles undamaged skin histologically, but without epidermal adnexal structures. Six weeks after application to full thickness skin defects, the composite replacements had closed the wounds and allowed the restoration of full thickness skin (FIG. 7). The reticular pattern in the dermal component of the repaired skin represents areas where the dermal membrane had not yet seen replaced completely by regenerating connective tissue. The repaired epidermis was very well organized, stratified, and differentiated, but contained no rete pegs or epidermal adnexal structures.

Success of grafts containing cultured HK also depends on the ability of the cultured cells to continue to proliferate indefinitely in analogy to epidermal stem cells. Earlier studies combined cultured HK sheets with collagen-GAG dermal membranes in vitro and resulted in no attachment of the HK sheets to the dermal membranes in a variety of culture conditions. Following these results, cell growth assays revealed that confluent sheets of HK cells have greatly reduced growth potential compared to subconfluent cultures. This finding is consistent with the "density inhibition" of confluent HK cultures as they proceed from exponential growth phase (actively growing, subconfluent) into stationary growth phase (growth arrested, confluent sheets); Wille et al, *J. Cell Physiol.* 121:31–44 (1984); Pittelkow et al, *J. Invest. Dermatol.* 86:401–417 (1986). Failure of HK cells sheets to attach to the membrane reflects loss of growth potential associated with growth arrest after transition into the stationary growth phase. Subsequently HK cultures in exponential growth phase were inoculated directly onto dermal membrane and found to attach readily and continue to grow to form continuous cell sheets. The use of HK in exponential growth phase on dermal membranes not only retain growth potential as demonstrated by the presence of mitotic cells in the composite grafts, but also were capable of producing their own hemidesmosomes, extracellular matrix, and collagen for attachment to the collagen-GAG membrane. The retention of growth potential by preparation of composite grafts with HK cells in exponential growth phase may be expected to increase the proportion of cells in the graft that are capable of long-term proliferation after application to the wound, in analogy to keratinocyte stem cells in undamaged epidermis.

Although long-term proliferation is of central importance to the permanence of the cultured graft, some epidermal stratification is also desirable to reduce the graft's fragility and to help protect the proliferative cells from mechanical damage. The addition of fetal bovine serum (FBS) to the culture conditions promoted epidermal stratification and differentiation, but also allowed continued cell division as demonstrated by the presence of mitotic HK within the partially stratified epidermal component of the composite graft. However, FBS has been shown to greatly inhibit the growth in vitro of HK. Pittelkow et al, *J. Invest. Dermatol.* 86:410–417 (1986). Reduced growth and increased differentiation in the presence of FBS is comparable to the regulation of HK growth rate and differentiation by calcium ion concentration in serum-free and in biochemically defined culture media. Boyce and Ham, *J. Invest. Dermatol.* 81(1), suppl.: 335–405 (1983); Wille et al, *J. Cell Physiol.* 121:31–44 (1984). Therefore, the degrees of continued HK proliferation and HK stratification may be adjusted as functions of the concentrations of FBS and calcium ion in the culture medium. However, the effect of density inhibition of HK proliferation after confluency on the dermal membrane will reduce cellular growth rate independent of the effects of FBS or calcium ion concentrations.

EXAMPLE III

Efficacy of composite skin grafts consisting of collagen-glycoasaminoglycan dermal substitutes and cultured human epidermal keratinocytes is tested by application to full-thickness skin wounds (2×2 cm to a depth of the paniculus carnosis) on congenitally athymic balb/c mice. Treated wounds are dressed sterilely with a combination of non-stick materials such as polypropylene mesh contacting the grafts and the wound. The grafts are then covered on the surface exposed to the environment with sterile, vapor-permeable materials, for example vaseline impregnated gauze. Wound treatment with composite grafts is compared to treatment with murine autograft, human xenograft, or no graft after six weeks of observation. Persistence of cultured human epidermal cells may be used as an indication of acceptance of the cells and is verified by staining of histological sections of repaired skin with antibodies against human histocompatibility antigens (HLA-ABC). Preliminary results demonstrate This staining is obtained as expected. Rate of acceptance of cultured human cells is determined as:

repair wounds positive for HLA-ABC×100=% ACCEPTANCE all wounds treated with composite grafts Wound contraction provides an index of scarring, and is measured directly by rectilinear planimetry of photographs of repaired wounds. Quantitative data from wound size measurements allows statistical analysis of wound contraction. Positive correlation of reduced wound contraction with increased acceptance of composite grafts provides an index by which efficacy of composite grafts in treatment of full-thickness skin wounds, with minimal scarring, may be demonstrated.

EXAMPLE IV

Biotinylation of Collagen

Biotin-N-hydroxysuccinimide (BNHS) was covalently bound to collagen using modifications of the procedure described by Guesdon et al., *J. Histochem. Cytochem.* 27(8): 1131–1139 (1979). Briefly, BNHS (Sigma Chem. Co., St. Louis, Mo.; Cat. No. H1759) was dissolved at a concentration of 0.1 M in dimethyl formamide and mixed with solubilized collagen at an approximate molar ratio of 10:1 and allowed to react for 1 hour at room temperature. The mixture was dialysed for 24 hours at 4° C. against several changes of phosphate buffered saline (PBS). After dialysis, the biotinylated collagen was mixed 1:1 with glycerol and stored at −20° C. until used.

Spot Test With Avidin-Horseradish Peroxidase (HRP).

Biotinyleted collagen or non-biotinylated collagen was diluted 1:3, 1:5, 1:10 and 1:30 using 0.05 M Tris-Cl buffer, pH 7.6. Next, 3 µl of each dilution was spotted onto nitrocellulose (NC) paper and allowed to air dry according to the spot test for detecting HRP covalently bound to avidin (avidin-HRP) described by Boorsma et al., *Histochemristry* 84:333–3337 (1986), incorporated by reference herein. NC paper was wetted with 0.05% Tween 20 in PBS (Tween-PBS) followed by two additional rinses with the same solution. The NC paper was drained, 5 μl of 0.1 to 1.0 mg/ml avidin-HRP were applied over each spot and incubated for 30 minutes. The NC paper was rinsed 3×10 minutes, flooded with a chromagen solution of 0.5 mg/ml diaminobenzidine in 0.05 M Tris, pH 7.6, containing 0.01% $H_2O_2$ (Graham et al., *J. Histochem. Cytochem.* 14(4):291–302 (1966), incorporated by reference herein) and allowed to develop. The reaction was quenched with Tween-PBS.

Figure 13:
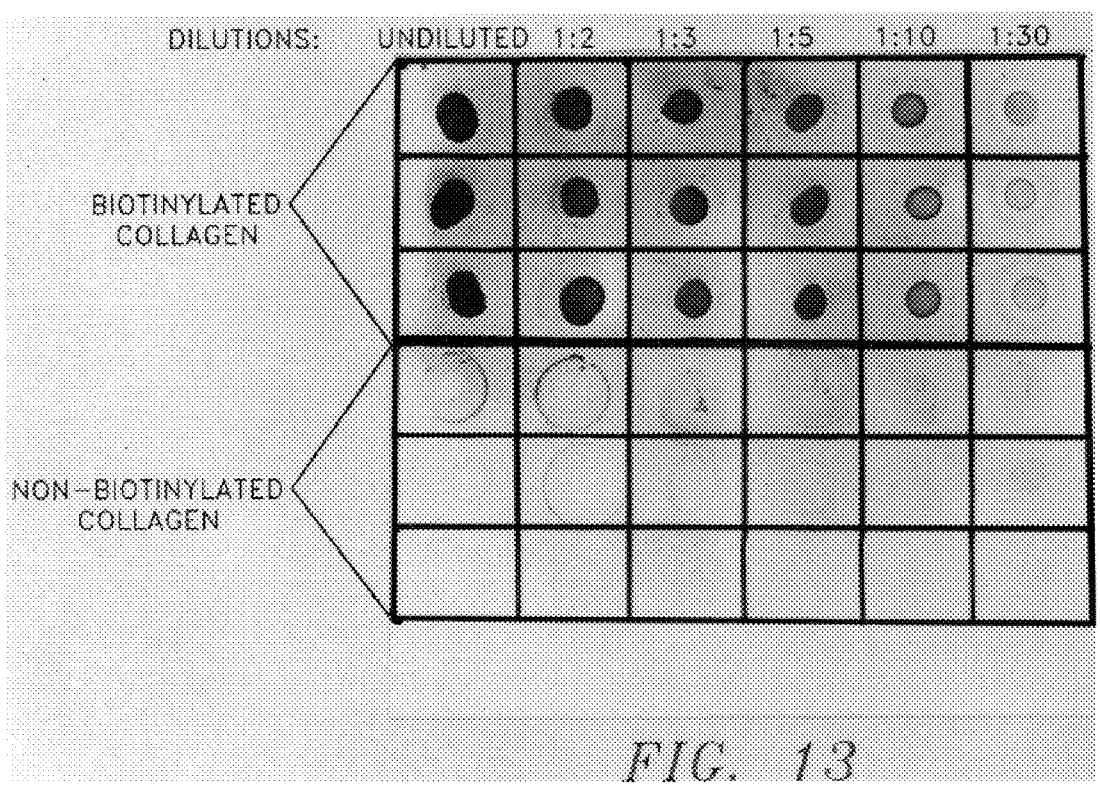
FIG. 13 is photographs of spot test results for binding of horseradish peroxidase (HRP) covalently bound to avidin with biotinylated collagen (A–C) and non-bio-tinylated collagen (D–F) on nitrocellulose paper as described in Example IV, infra.
Figure 14:
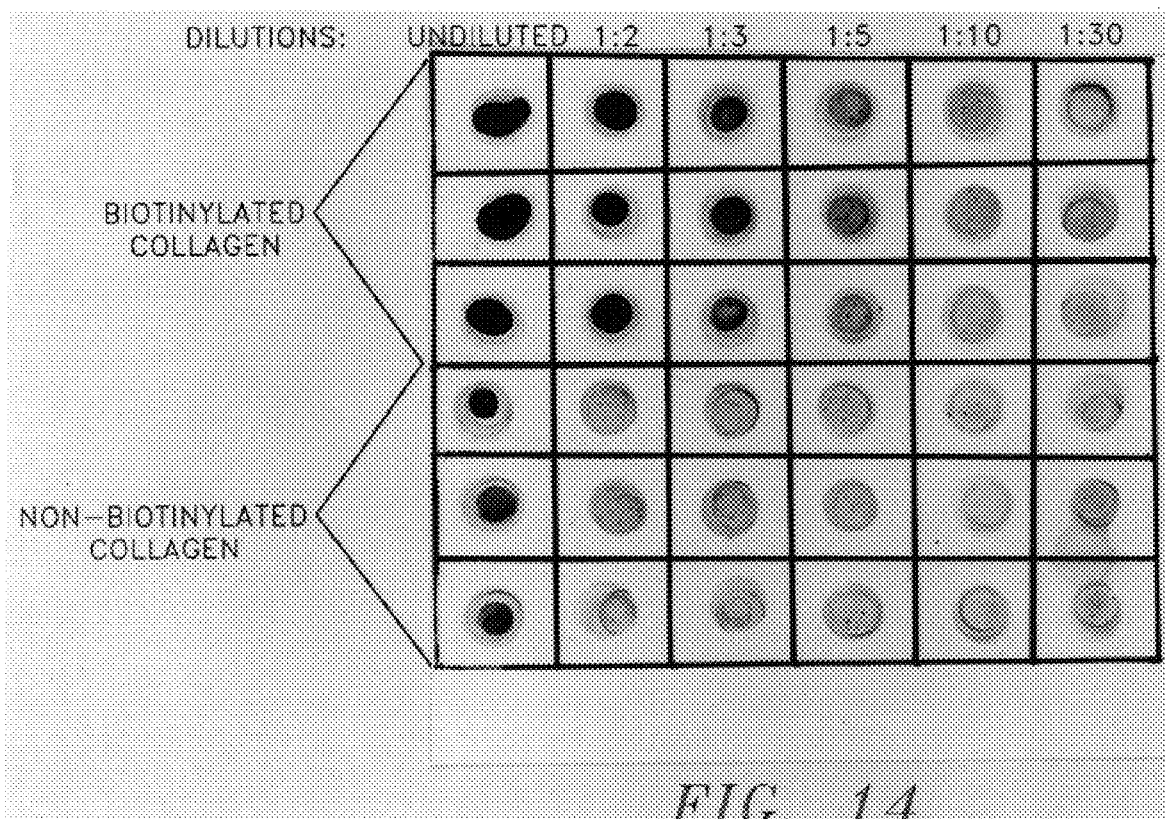
FIG. 14 is photographs of biotinylated HRP conjugated to biotinylated collagen.

FIG. 13 illustrates the spot test results for HRP covalently bound to avidin that was reacted with solubilized collagen, before and after biotinylation. Avidin-HRP became conjugated to and stained biotinylated collagen diluted 1:2, 1:3, 1:5 and 1:10 (FIGS. 13A and 13B) from a starting concentration of 0.15% wt/vol. Dilution of biotinylated collagen 1:30 showed a faint reaction with avidin-HRP and demonstrated the dilution of the conjugation substrate (FIG. 13C). No conjugation of avidin-HRP with non-biotinylated collagen occurred (FIGS. 13D, 13E and 13F), demonstrating the specific conjugation of avidin-HRP to biotinylated collagen.

EXAMPLE V

To demonstrate the ability of an active compound to be incorporated within the dermal membrane, solubilized collagen, before and after biotinylation was exposed to avidin followed by reaction with the enzyme HRP covalently bound to biotin (Sigma Chemical Co., St. Louis, Mo.) (FIGS. 12C and D). Biotin-HRP became conjugated to and stained biotinylated collagen after reaction with avidin, but did not become conjugated to non-biotinylated collagen that had been reacted with avidin. This further demonstrates the specificity of the conjugation of the avidin to biotinylated collagen. This also demonstrates the conjugation of biotinylated proteins to polyconjugal avidin molecules. If one of the biotinylated compounds is collagen in the form of a skin replacement, other biotinylated compounds may be conjugated by avidin to the skin replacement.

EXAMPLE VI

Solubilized collagen is biotinylated as described above in Example IV. Avidin is then added to conjugate with the biotin groups affixed to the collagen. Biotin covalently bound to biologically active molecules such as Fibroblast Growth Factor (FGF) is then allowed to conjugate with the avidin conjugated to the biotinylated collagen. HRP covalently bound to antibody, for example HRP bound to anti-FGF antibody (Massoglia, et al., *J. Cell. Physiol.* 132 (3): 31–537 (1987)) can be used to verify the conjugation of FGF to collagen by means of the biotin-avidin-biotin link (FIG. 12E). HRP-antibody is detected using the spot test described above in Example III, or may be quantitated spectrophotometrically in an assay format similar to the enzyme-linked immuno-sorbant assay (ELISA).

The dermal component having FGF incorporated, is then inoculated with the epidermal component of cultured human skin cells, as described in Example II, supra, to form a composite skin replacement. The composite is then tested by grafting to a wound in an animal model, for example athymic (nude) balb/c mice as described in Example II, supra, to determine the ability of the composite having biologically active molecules incorporated into the dermal membrane to promote skin repair and/or prevent wound infection. The results obtained for the composite are compared to those obtained from human xenograft, autograft and no graft, using wound contraction measurements as described in Example II, or determining persistence of cultured human epidermal cells in the composite replacement (Example III).

The covalent binding of moieties such as biotin to the dermal component of the replacement provides a mechanism for biochemical modification of the dermal component to promote cellular growth into and onto the biopolymer core of the skin substitute. For example, biologically active molecules such as FGF may be incorporated into the dermal membrane to promote wound healing, growth of new blood vessels (angiogenesis) and/or to reduce wound infection (sepsis). This combined with the above described regulation of the structure of the dermal membrane, permits structural and biochemical optimization of dermal-epidermal skin replacements for wound repair.

As will be apparent to those skilled in the art in which the invention is addressed, the present invention may be embodied in forms other than those specifically disclosed above without departing from the spirit or potential characteristics of the invention. Particular embodiments of the present invention described above are therefore to be considered in all respects as illustrative and not restrictive. The scope of the present invention is as set forth in the appended claims and equivalents thereof rather than being limited to the examples contained in the foregoing description.

What is claimed is:

1. A composite skin replacement comprising:
   a) a layer of cultured epidermal cells;
   b) a dermal membrane component; and
   c) a substantially non-porous lamination layer on one surface of said porous dermal membrane component.

2. A composite skin replacement comprising:
   a) a layer of cultured epidermal cells; and
   b) a porous resorbable dermal membrane component formed from collagen or collagen and mucopolysaccharide compounds, said dermal membrane component laminated with a solution containing from about 0.52% to about 2% weight/volume of collagen or a mixture of collagen and mucopolysaccharide compounds and from about 0.1% to about 10% volume/volume of a volatile cryoprotectant to form a laminating solution present on the flat surface at up to 0.06 ml/cm$^2$.

3. A composite skin replacement comprising:
   a) a layer of cultured epidermal cells;
   b) a porous, resorbable dermal membrane component formed from collagen or collagen and mucopolysaccharide compounds; and
   c) a substantially non-porous lamination layer on one surface of said porous dermal membrane component located between said dermal membrane component and said epidermal component to promote localization of epidermal cells on the surface of said dermal membrane component and to promote movement of nutrients to the cells of the cellular epidermal component, said lamination layer formed with a solution containing from about 0.52% to about 2% weight/volume of collagen or a mixture of collagen and mucopolysaccharide compounds and from about 0.1% to about 10% volume/volume of a volatile cryoprotectant to form a laminating solution present on the flat surface at up to 0.06 ml/cm$^2$.

4. A composite skin replacement comprising:

a) a cultured cellular epidermal layer;

b) a porous, resorbable dermal membrane component comprising collagen; and c) a substantially non-porous lamination layer, wherein said non-porous lamination layer contains collagen which is solubilized in a solution with a cryoprotectant, and is located between said dermal membrane component and said epidermal cellular layer to promote localization of epidermal cells on the surface of said dermal membrane component and to promote movement of nutrients to the cells of the cellular epidermal layer.

5. A method for delivering biologically active molecules to an implantation site to release therapeutic drugs comprising:

a. attaching biologically active molecules to the composite skin replacement of claim 1; and b. grafting the composite of (a) to an implantation site of damaged skin so that the biologically active molecules can be delivered to the implantation site.

6. The method of claim 5, wherein said biologically active molecules are selected from the group consisting of growth factors, hormones, anti-inflammatory agents and antibiotic agents.

7. The method of claim 6, wherein said biologically active molecules are growth factors selected from the group consisting of Fibroblast Growth Factor and Epidermal Growth Factor.

* * * * *